United States Patent [19]

Rajagopalan

[11] 4,438,120

[45] Mar. 20, 1984

[54] PYRIDOINDOLOBENZODIAZEPINE TRANQUILIZERS

[75] Inventor: Parthasarathi Rajagopalan, Wilmington, Del.

[73] Assignee: E. I. Du Pont de Nemours & Company, Wilmington, Del.

[21] Appl. No.: 441,376

[22] Filed: Nov. 12, 1982

[51] Int. Cl.$^3$ .................... A61K 31/55; C07D 471/14
[52] U.S. Cl. .............................. 424/256; 260/239.3 P; 260/239.3 T; 346/48
[58] Field of Search .................. 260/239.3 P, 239.3 T; 346/48; 424/256

[56] References Cited

U.S. PATENT DOCUMENTS

| 3,373,168 | 3/1968 | Cohen et al. | 546/48 |
|---|---|---|---|
| 3,457,271 | 7/1969 | Cohen et al. | 546/48 |
| 3,764,684 | 10/1973 | Finizio | 546/48 |
| 3,790,675 | 2/1974 | Blumberg | 546/48 |
| 3,829,431 | 8/1974 | Berger et al. | 546/48 |
| 3,890,327 | 6/1975 | Berger | 546/48 |
| 3,932,650 | 1/1976 | Adams | 546/48 |
| 3,983,123 | 9/1976 | Adams | 546/48 |
| 4,018,930 | 4/1977 | Berger | 546/48 |

OTHER PUBLICATIONS

Linnell and Perkin, J. Chem. Soc., 125 (1924), pp. 2451-2460

Primary Examiner—Robert T. Bond

[57] ABSTRACT

Pyridoindolobenzodiazepines, including 1,2,3,4-tetrahydropyrido[4',3':2,3]indolo[1,7-ab][1,4]benzodiazepine-9(8H)-ones and 1,2,3,4,8,9-hexahydro- and 1,2,3,4,4a,8,9,14a-octahydropyrido[4',3':2,3]indolo[1,7-ab][1,4]benzodiazepines, are useful as tranquilizers.

14 Claims, No Drawings

PYRIDOINDOLOBENZODIAZEPINE TRANQUILIZERS

BACKGROUND OF THE INVENTION

1. Field of Invention

This invention relates to pyridoindolobenzodiazepines, processes for their preparation and uses as tranquilizers, and more particularly to tetrahydro-, hexahydro-, and octahydropyridoindolobenzodiazepines useful as tranquilizers.

2. Prior Art

Cohen et al., U.S. Pat. Nos. 3,373,168, and 3,457,271, describe compounds which are 1,2,3,4,8,9-hexahydropyrido[4',3':2,3]indolo[1,7-ab][1]benzazepines and 1,2,3,4,4a,8,9,14a-octahydropyrido[4',3':2,3]indolo[1,7-ab][1]benzazepines and their preparation from N-nitrosoiminodibenzyl and 1-alkyl-4-piperidones.

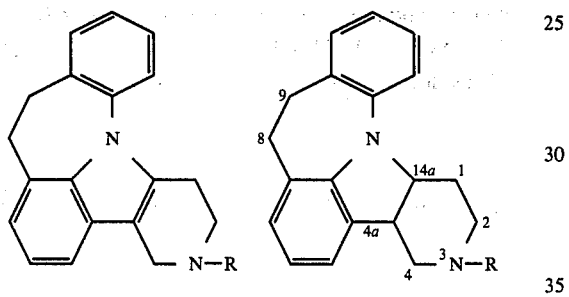

The octahydro compounds are said to be antidepressant agents.

Adams, in U.S. Pat. Nos. 3,932,650 and 3,983,123, describes CNS depressant and analgesic 1,2,3,4,4a,8,9,-14a-octahydropyrido[4',3':2,3]indolo[1,7-ab][1]benzazepines. These compounds are 4a,14a-trans, while the octahydro compounds of the above patent are of the cis configuration.

Berger, in U.S. Pat. Nos. 3,890,327 and 4,018,930, describes trans-1,2,3,4,4a,8,9,14a-octahydropyrido[4',3':2,3]indolo[1,7-ab][1]benzazepine and 3-substituted analgesic and sedative/tranquilizer derivatives thereof.

Blumberg, U.S. Pat. No. 3,790,675 and Finizio, U.S. Pat. No. 3,764,684, describe analgesic, antiolytic, and antipsychotic 1,2,3,4,8,9-hexahydropyrido[4',3':2,3]indolo[1,7-ab][1]benzazepines.

A process for preparing these hexahydropyridoindolobenzazepines is claimed in Berger and Teller U.S. Pat. No. 3,829,431. It involves N-nitrosoiminodibenzyl and 4-piperidone or 1-allyl-4-piperidones.

In an article by W. H. Linnell and W. H. Perkin, Jr., *J. Chem. Soc.*, 2451–2460 (1924), the parent, unsubstituted nitroso compound (III) described in the subject application is prepared and reacted with cyclohexanone to give a product with one of the following structures:

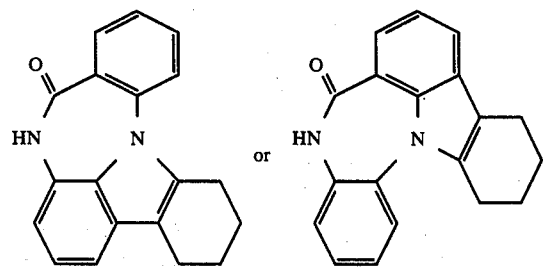

Linnell et al. preferred the latter structure on the basis of some degradative work, but by analogy to the behavior of 4-piperidone in the present application, the former might be expected to have been the actual product.

SUMMARY OF THE INVENTION

According to the present invention there is provided a compound of the formula:

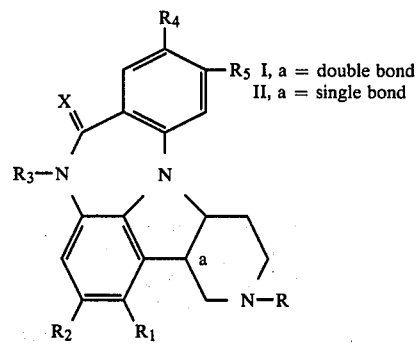

wherein
a is a single or double bond; provided that when a is a single bond, the ring fusion is of the trans-configuration;

$R_1$, $R_2$, $R_4$ and $R_5$ independently are H, alkyl of 1 or 2 carbon atoms, $CF_3$, Cl, F or Br;

$R_3$ is H or alkyl of 1 to 3 carbon atoms;

R is H, alkyl of 1 to 10 carbon atoms, $(CH_2)_nC(O)R_6$, $(CH_2)_nCH(OH)R_6'$, $(CH_2)_nCONR_8R_9$, $(CH_2)_n(C_{3-7}$ cycloalkyl), $(CH_2)_n$adamantyl,

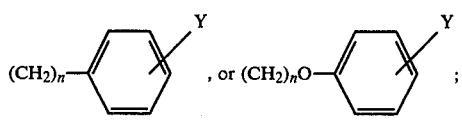

n is 1 to 8;

$R_6$ is H, OH, $OR_7$, $C_{1-3}$ alkyl, $C_{3-6}$ cycloalkyl, or

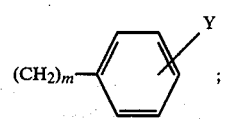

$R_6'$ is H, $C_{1-3}$ alkyl, $C_{3-6}$ cycloalkyl, or

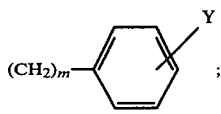

m is 0 to 3;
$R_7$ is $CH_3$ or $C_2H_5$;
Y is H, $CH_3$, $OCH_3$ or $NO_2$;
$R_8$ and $R_9$ are independently H, $CH_3$ or $C_2H_5$, or
$R_8$ and $R_9$, together, are $-CH_2CH_2OCH_2CH_2-$; and
X is $H_2$, O, or S, provided that when X is O or S, then a is a double bond; and provided further that when X is $H_2$, a is a single bond, and $R_1$, $R_4$ and $R_5$ are H, then $R_2$ cannot be $CF_3$ when R is $CH_3$ or

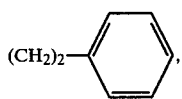

and $R_2$ cannot be Cl when R is

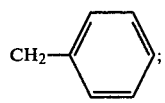

or a pharmaceutically acceptable salt thereof.

Certain of the compounds of the formula are capable of resolution into their optical antipodes. In these cases, this invention includes the racemates, the dextrorotatory and levorotatory antipodes, and preparations enriched in one or the other of the antipodes.

This invention also provides pharmaceutical compositions containing compounds of the above formula, and methods of using these compounds as tranquilizers in mammals. The tetrahydro and hexahydro compounds which are not active tranquilizers may serve as intermediates to active octahydro compounds.

This invention further provides novel 10,11-dihydro-5-nitrosodibenzo[b,e][1,4]diazepin-11(5H)-ones of Formula III

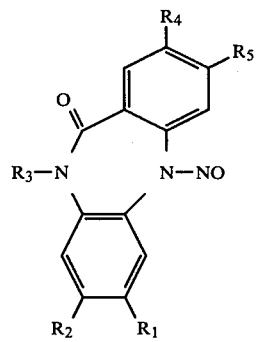

where $R_1$, $R_2$, $R_3$, $R_4$, and $R_5$ are as defined above, useful in preparing compounds of Formula I and II.

This invention also provides an intermediate compound of the formula:

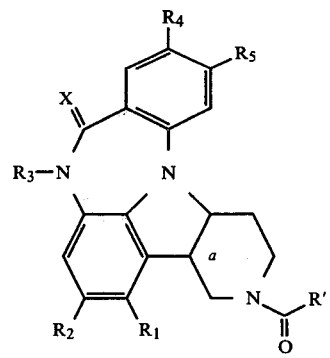

I' (R=COR'), a = double bond
II' (R=COR'), a = single bond wherein
a, $R_1$, $R_2$, $R_4$, $R_5$, $R_7$, X, Y, and n are as defined above;
$R_3$ is H, alkyl of 1 to 3 carbon atoms, or $CO_2R_7$; and
R' is $OR_7$, alkyl of 1 to 9 carbon atoms, $(CH_2)_{n-1}(C_{3-7}$ cycloalkyl), $(CH_2)_{n-1}$ adamantyl,

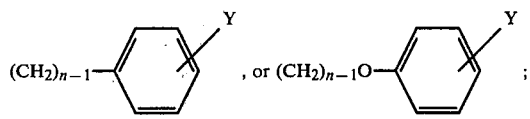

useful for preparing compounds of Formulae I and II with certain 3-substituents, R.

PREFERRED COMPOUNDS

Preferred compounds of Formulae I and II are those in which:
R is alkyl of 1 to 3 carbon atoms, or
$R_1$ is H, or
$R_2$ is Cl, or
$R_3$ is H or $CH_3$, or
$R_4$ is Cl, or
$R_5$ is H.

Compounds of Formula II are preferred over compounds of Formula I in which X=$H_2$, which, in turn, are preferred over compounds of Formula I in which X=O, which, in turn, are preferred over compounds of Formula I in which X=S.

Specifically preferred, because of pharmacological potency, is trans-6-chloro-3-ethyl-1,2,3,4,4a,8,9,14a-octahydropyrido[4',3':2,3]indolo[1,7-ab][1,4]benzodiazepine and pharmaceutically acceptable salts thereof, particularly the dihydrochloride salt.

NOMENCLATURE

The numbering and nomenclature used herein for the compounds of this invention are shown in the following structures:

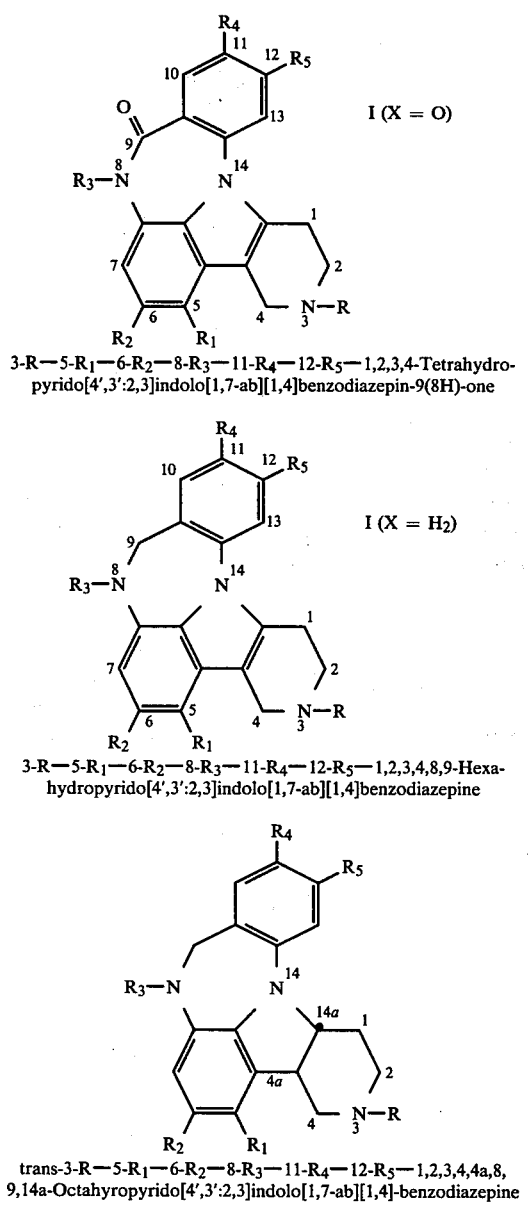

3-R—5-$R_1$—6-$R_2$—8-$R_3$—11-$R_4$—12-$R_5$—1,2,3,4-Tetrahydro-pyrido[4',3':2,3]indolo[1,7-ab][1,4]benzodiazepin-9(8H)-one 3-R—5-$R_1$—6-$R_2$—8-$R_3$—11-$R_4$—12-$R_5$—1,2,3,4,8,9-Hexahydropyrido[4',3':2,3]indolo[1,7-ab][1,4]benzodiazepine trans-3-R—5-$R_1$—6-$R_2$—8-$R_3$—11-$R_4$—12-$R_5$—1,2,3,4,4a,8,9,14a-Octahyropyrido[4',3':2,3]indolo[1,7-ab][1,4]-benzodiazepine

DETAILED DESCRIPTION OF THE INVENTION

Starting materials for preparing compounds of this invention are novel 10,11-dihydro-5-nitrosodibenzo[-be][1,4]diazepin-11(5H)-ones of Formula III. The nitroso compounds of Formula III are prepared by the sequence of reactions shown in Scheme I, where X is Cl, Br, or I, but preferably chloro. Choice of appropriate halonitrobenzene (IV) and anthranilic acid (V) reaction partners allows for variation of substituents $R_1$, $R_2$, $R_4$, and $R_5$. This procedure for preparing the 10,11-dihydrodibenzo[be][1,4]diazepine-11(5H)-ones VIII, which are precursors to III, is that of F. Hunziker et al., *Arzneimittel-Forschung*, 13, 324-8 (1963). The nitrosation procedure is a standard one, similar to that used in Cohen et al. (op. cit.). Alkylation of the nitroso compound III where $R_3$ is H provides III where $R_3$ is alkyl. The $R_3$ group may alternatively be introduced at later stages of the synthesis.

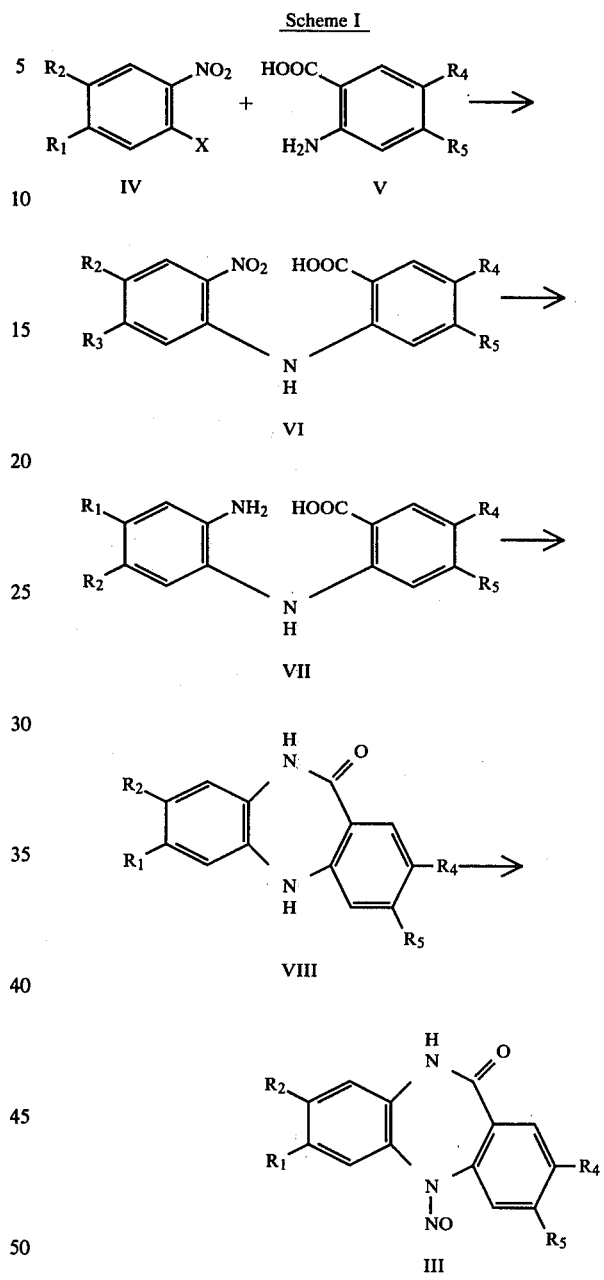

Scheme I

Compounds I where X=O are prepared by reducing III with an agent such as zinc dust in the presence of an acid such as acetic acid, the product being condensed in situ with an unsubstituted or 1-substituted-4-piperidone. The resulting hydrazone is converted to its hydrochloride salt which is then heated in the presence of an alcohol such as 2-propanol at a temperature between 80° and 110° C. to yield a compound of Formula I where X=O. In this reaction, R may not be $(CH_2)_nCOR_6$. This group must be introduced at a later stage as described below.

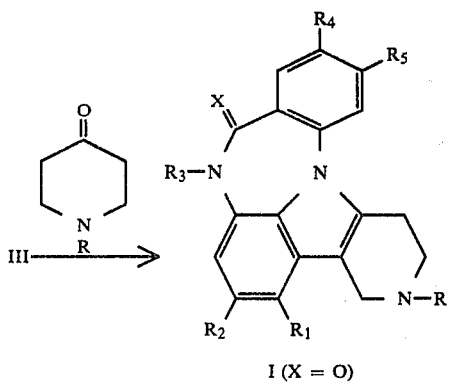

I (X = O)

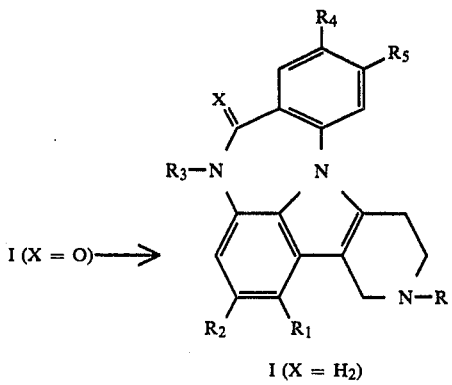

I (X = H₂)

The desired 3-substituents, R, can be introduced into the nor compound by alkylation, by acylation and subsequent reduction, or by Michael reaction of the 3-nitrogen.

For example, a compound of Formula I (X=O; R=H) can be alkylated with an alkyl halide such as 2-bromopropane in the presence of a base such as potassium carbonate in a solvent such as dimethylformamide at a temperature between 50° to 100°, to provide a compound of Formula I (X=O) where R=alkyl, i.e., 2-propyl.

A compound of Formula I (X=O; R=H) can be condensed with an α,β-unsaturated carbonyl compound such as methyl vinyl ketone in a solvent such as dimethylformamide at a temperature between 20° to 80° C. to yield a compound of Formula I (X=O) where R=(CH₂)₂COCH₃.

A compound of Formula I (X=O; R=H) can be acylated at the 3-position with an acid chloride (R'COCl) such as benzoyl chloride (R'=Ph), in the presence of a base such as triethylamine, in a solvent such as dimethylformamide, and at a temperature between 20° to 80° C. to yield a compound of Formula I' (X=O) where R'=Ph. This acyl compound is reduced to the corresponding alkyl compound in a later reduction step. This method is not suitable for introduction of a group resulting from reduction of a 3-acyl group into compounds of the invention of Formula I (X=O), since I (X=O) is reduced to I (X=H₂) or to II under conditions required for reduction of the 3-acyl group. When compounds of Formula I (X=H₂) or II are desired, however, several desired transformations may be accomplished in a single process step. The 3-acyl compound where R' is OR₇ is a carbamate, and provides the 3-methyl compound on reduction.

3-Substituents R may be introduced by the same procedures into compounds I (X=H₂) and II, starting from the corresponding nor compounds, I (X=H₂, R=H) and II (R=H).

A compound of Formula I (X=H₂) is prepared from a compound of Formula I (X=O) by reduction with an agent such as lithium aluminum hydride in a suitable solvent such as tetrahydrofuran at a temperature between 20° to 80° C.

Alternatively, a compound of Formula I (X=O; R=H) can be treated with borane in tetrahydrofuran and the amine-borane complex formed can be isolated and heated with 1-octene in the presence of xylene (optional) at a temperature between 100°-150° C. to yield a compound of Formula I (X=H₂).

To prepare a compound of Formula II, a compound of Formula I (X=H₂; R≠H) is first treated with an agent such as diborane in a solvent such as tetrahydrofuran at a temperature between 20° to 80° C. The resulting amine-borane complex is treated with an acid such as hydrochloric acid at a temperature between 20° to 110° C. to provide a compound of Formula II.

Compounds of Formula I (X=S) are prepared from compounds of Formula I (X=O) by sulfurization with a reagent such as P₄S₁₀. Sulfur may also be introduced at an earlier stage of the synthesis, i.e., by sulfurization of III or VIII.

The preparation of the compounds of the invention is described in detail in the examples which follow. All temperatures, reported in degrees Centigrade, are uncorrected. Percentages are by weight, but proportions of solvent mixtures are by volume. The following abbreviations are used: Me=methyl, Et=Ethyl, Pr=propyl, Ph=phenyl, and THF=tetrahydrofuran.

EXAMPLE I-1

Preparation of 10,11-Dihydro-5-nitrosodibenzo[be][1,4]diazepin-11(5H)-one (III, R₁=R₂=R₄=R₅=H)

A solution of sodium nitrite (27 g) in water (60 ml) was added, in one lot, to a stirred solution of 10,11-dihydrodibenzo[be][1,4]diazepin-11(5H)-one (84.6 g) in glacial acetic acid (1 liter) and the resulting mixture stirred for 2 hours at room temperature and filtered. The title product was washed thoroughly with water, pressed dry and air-dried. The material melting at 175°-185° (dec.) is pure enough for the next step. A small quantity was recrystallized from methanol to yield the title compound, m.p. 175°-185° (dec.).

The compound of Example I-1, other substituted 10,11-dihydro-5-nitrosodibenzo[be][1,4]diazepin-11(5H)-ones which were prepared by essentially the procedure of Example I-1, and other compounds which can be prepared by the same procedure are listed in Table IA.

TABLE IA

Structure III: A tricyclic compound with substituents $R_1$, $R_2$ on one ring, $R_4$, $R_5$ on another ring, with HN, C=O, and N-NO groups.

| Example | $R_1$ | $R_2$ | $R_4$ | $R_5$ | m.p. (Solvent of recrystallization) |
|---|---|---|---|---|---|
| I-1 | H | H | H | H | 175–185° (MeOH)* |
| I-2 | Cl | H | H | H | 180–190° (MeOH)* |
| I-3 | H | Cl | H | H | 235–245° (EtOH)* |
| I-4 | H | H | Cl | H | 264–266° (MeOH)* |
| I-5 | H | H | H | Cl | 175–185° (MeOH)* |
| I-6 | H | CF$_3$ | H | H | 175–185° (EtOH)* |
| I-7 | H | H | Me | H | 175–180° (EtOH/MeOH)* |
| I-8 | H | Cl | Me | H | 188–190° (EtOH/MeOH)* |
| I-9 | H | CF$_3$ | Cl | H | 175–185° (EtOH)* |
| I-10 | Et | H | F | H | |
| I-11 | Et | H | CF$_3$ | H | |
| I-12 | H | Et | H | Me | |
| I-13 | H | Br | H | Br | |
| I-14 | H | F | CF$_3$ | H | |
| I-15 | H | F | H | CF$_3$ | |
| I-16 | H | CF$_3$ | Et | H | |
| I-17 | Br | H | CF$_3$ | H | |
| I-18 | Me | H | F | H | |

*this material melted with decomposition

EXAMPLE I-19

Preparation of 10,11-dihydro-10-methyl-5-nitrosodibenzo[b,e][1,4-]diazepin-11(5H)-one (III, $R_3$=CH$_3$, $R_1$=$R_2$=$R_4$=$R_5$=H)

Sodium hydride (2.4 g, 50% oil dispersion) was added in small portions to a water cooled solution of 10,11-dihydro-5-nitrosodibenzo[b,e][1,4]diazepin11(5H)-one (13.5 g) in dimethylformamide (200 ml) such that the temperature did not exceed 20° C. After the addition was complete the mixture was stirred at room temperature for 30 minutes and then treated with methyl iodide (7.0 g) added in one lot. The resulting mixture, after being stirred at room temperature for 2 hours, was poured into an excess of ice and water, and extracted with methylene chloride. The methylene chloride extract was washed with water, dried over magnesium sulfate and the solvent evaporated under reduced pressure. The residue, which contained some dimethylformamide, was repeatedly triturated with water until it turned to a crystalline solid. It was filtered off, washed with water and air-dried to yield the title compound, m.p. 95°–98°.

Using the procedure of Example I-19, but substituting various functionalized 10,11-dihydro-5-nitrosodibenzo[b,e][1,4]diazepin-11(5H)-ones for the unsubstituted nitroso compound used in Example I-19 and varying the alkylating agent, the 10-substituted derivatives listed in Table IB can be prepared.

TABLE IB

| Ex. | $R_1$ | $R_2$ | $R_3$ | $R_4$ | $R_5$ | Starting Material | Reagent |
|---|---|---|---|---|---|---|---|
| I-20 | Cl | H | Me | H | H | Ex. I-2 | Me$_2$SO$_4$ |
| I-21 | H | CF$_3$ | Et | H | H | I-6 | EtI |
| I-22 | H | Cl | Et | Me | H | I-8 | EtI |
| I-23 | H | CF$_3$ | 1-Pr | Cl | H | I-9 | 1-PrBr |
| I-24 | H | CF$_3$ | 2-Pr | Cl | H | I-9 | 2-PrI |

EXAMPLE 1

1,2,3,4-Tetrahydro-3-methylpyrido[4',3':2,3]indolo[1,7-ab][1,4]benzodiazepin-9(8H)-one (I, X=O; R=CH$_3$, $R_1$=$R_2$=$R_3$=$R_4$=$R_5$=H)

Zinc dust (130 g) was added in small portions to a vigorously stirred and cooled mixture of 10,11-dihydro-5-ntirosodibenzo[be][1,4]diazepin-11-one (Example I-1; 55 g), 1-methyl-4-piperidone hydrochloride (34 g), absolute ethanol (750 ml) and glacial acetic acid (800 ml) such that the temperature did not rise above 5° C. After the addition was complete the mixture was stirred for 90 minutes at room temperature and filtered. The residue was washed with a small quantity of absolute ethanol and the filtrates combined and heated on the steam bath for 1 hour. The mixture was then concentrated to about one third of its volume and added to vigorously stirred and cooled ammonium hydroxide (28–30%, 400 ml). The mixture was extracted twice with methylene chloride and the combined methylene chloride extracts washed with water, dried over anhydrous magnesium sulfate and stripped of the solvent under reduced pressure to yield a viscous liquid which was dissolved in the requisite quantity of anhydrous tetrahydrofuran and added to an excess of absolute ether saturated with gaseous hydrogen chloride. The salt that separated was filtered off, washed with ether, suspended in 2-propanol (1 liter), stirred and refluxed for 48 hours. The mixture was then cooled and filtered and the product washed successively with small quantities of 2-propanol and finally with ether to yield the title compound as its hydrochloride, m.p. 305°–307° C. (dec.).

The title compound (the free base) was obtained by treating the hydrochloride with excess ammonium hydroxide, extracting the mixture with methylene chloride, washing the methylene chloride extract with H$_2$O, drying it over anhydrous magnesium sulfate, removal of the solvent under reduced pressure and recrystallizing the residue from a mixture of 2-propanol and methanol, m.p. 222°–225° (dec.).

The compound of Example 1, other 1,2,3,4-tetrahydropyrido[4',3':2,3]indolo[1,7-ab][1,4]benzodiazepin-9(8H)-ones which were prepared by essentially the foregoing procedure, varying the 4-piperidone and the 10,11-dihydro-5-nitrosodibenzo[be][1,4]diazepin-11-one reactants, and other compounds which can be prepared by the same procedure are listed in Table II.

TABLE II (Structure I shown with substituents R, R₁, R₂, R₃, R₄, R₅; X = O)

| Ex. | R | R₁ | R₂ | R₃ | R₄ | R₅ | m.p. (Solvent of recrystallization) |
|---|---|---|---|---|---|---|---|
| 1 | Me | H | H | H | H | H | 222–225° (2-PrOH/MeOH)* |
| 2+ | H | H | H | H | H | H | 323–326° (MeOH)* |
| 3+ | H | Cl | H | H | H | H | 313–315° (MeOH)* |
| 4 | H | H | Cl | H | H | H | 223–225° (THF)* |
| 5 | H | H | CF₃ | H | H | H | 220–222° (2-PrOH/EtOH)* |
| 6 | H | H | H | H | Me | H | 230–232° (MeOH)* |
| 7 | H | H | H | H | Cl | H | 260–267° (MeOH/THF)* |
| 8 | H | H | H | H | H | Cl | 263–265° (MeOH)/THF)* |
| 9 | H | Cl | H | H | Me | H | 215–217° (2-PrOH/MeOH)* |
| 10 | Me | Cl | H | H | H | H | 235–237° (EtOH/MeOH)* |
| 11 | Me | H | Cl | H | H | H | 227–230° (MeOH)* |
| 12 | Me | H | H | H | Cl | H | 238–240° (2-PrOH/MeOH)* |
| 13 | Me | H | Cl | H | Me | H | 260–263° (MeOH/THF)* |
| 14 | Me | H | Cl | H | Cl | H | 280–283° (THF)* |
| 15 | Me | H | H | H | H | Cl | 282–285° (MeOH/THF)* |
| 16 | C₆H₅(CH₂)₂ | H | Cl | H | Me | H | 190–193° (2-PrOH/EtOH)* |
| 17 | Me | H | CF₃ | H | Cl | H | 248–250° (2-PrOH)* |
| 18 | Me | H | CF₃ | H | H | H | 283–285° (MeOH)* |
| 19 | Me | Cl | H | H | Me | H | 294–297° (THF)* |
| 20 | H | H | Cl | H | Me | H | 245–248° (THF)* |
| 21 | H | H | CF | H | Cl | H | 285–287° (MeOH)* |
| 22 | n-Decyl | H | Cl | H | H | H | |
| 23 | cyclopropyl-CH₂ | H | CF₃ | H | H | H | |
| 24 | cyclohexyl-(CH₂)₃ | H | H | Me | CF₃ | H | |
| 25 | Adamantyl-(CH₂)₅ | H | Cl | Me | H | CF₃ | |
| 26 | 4-CH₃OC₆H₄(CH₂)₂ | H | Me | H | Cl | H | |
| 27 | 3-NO₂C₆H₄(CH₂)₃ | H | Cl | H | CF₃ | H | |
| 28 | 4-CH₃C₆H₄(CH₂)₂ | Cl | H | H | H | H | |
| 29 | PhCH₂ | H | H | H | H | Cl | |
| 30 | 4-CH₃OC₆H₄O(CH₂)₄ | H | H | H | Cl | H | |

*this compound melted with decomposition
+hydrochloride salt

EXAMPLE 31

1,2,3,4-Tetrahydro-3-(2-propyl)pyrido[4',3':2,3]indolo[1,7-ab][1,4]benzodiazepin-9(8H)-one (I; X=O; R=2-Pr, R₁=R₂=R₃=R₄=R₅=H)

Anhydrous potassium carbonate (2.8 g) and 2-bromopropane (2.4 g) were added to a warm solution of 1,2,3,4-tetrahydropyrido[4',3':2,3]indolo[1,7-ab][1,4]benzodiazepin-9(8H)-one (Example 2; 5.8 g) in dimethylformamide (50 ml) and the resulting mixture was stirred and heated at 85°–90° for 24 hours, cooled and poured into an excess of ice and water. The solid that separated was filtered off, washed thoroughly with water and recrystallized from methanol to yield the title compound, m.p. 318°–320° (dec.).

The compound of Example 31, 3-substituted compounds prepared by essentially the procedure of Example 31, and other compounds which can be prepared by that procedure are listed in Table III.

TABLE III

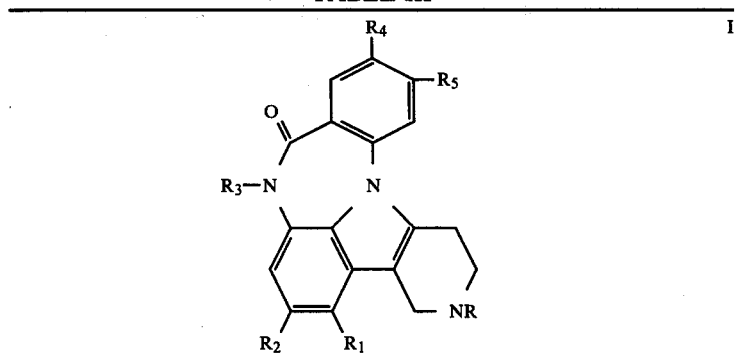

(X = O)

| Ex. | R | $R_1$ | $R_2$ | $R_3$ | $R_4$ | $R_5$ | m.p. (Solvent of recrystallization) |
|---|---|---|---|---|---|---|---|
| 31 | 2-Pr | H | H | H | H | H | 318–320° (MeOH) |
| 32 | Et | H | H | H | H | H | 260–265° (MeOH) |
| 33 | 1-Pr | Cl | H | H | H | H | 185–188° (MeOH) |
| 34 | 1-Pr | H | Cl | H | H | H | 239–241° (MeOH/THF) |
| 35 | 1-Hexyl | H | H | H | H | H | 205–207° (2-PrOH/MeOH) |
| 36 | 1-Hexyl | Cl | H | H | H | H | 173–175° (EtOH/MeOH) |
| 37 | 1-Hexyl | H | Cl | H | H | H | 285–288° (2-PrOH/MeOH) |
| 38 | ⌬-CH₂ (cyclohexylmethyl) | H | H | H | H | H | 200–203° (MeOH/THF) |
| 39 | (CH₂)₃CO₂Et | H | Cl | H | H | H | 275–277° (2-PrOH/THF) |
| 40 | F—C₆H₄—CO(CH₂)₃ | H | Cl | H | H | H | 255–260° (2-PrOH/MeOH) |
| 41 | 1-Hexyl | Cl | H | H | CH₃ | H | 145–148° (ether) |
| 42 | 1-Hexyl | H | Cl | H | CH₃ | H | 151–153° (2-PrOH/EtOH)* |
| 43 | 1-Hexyl | H | H | H | Cl | H | 248–250° (MeOH/THF)* |
| 44 | 1-Decyl | H | Cl | H | H | H | 140–145° (2-PrOH) |
| 45 | PhCH₂ | H | Cl | H | H | H | |
| 46 | ▷-CH₂ (cyclopropylmethyl) | H | H | H | H | Cl | |
| 47 | PhCOCH₂ | H | CF₃ | Me | H | H | |
| 48 | 4-F—C₆H₄COCH₂ | H | H | H | Cl | H | |
| 49 | Adamantyl-(CH₂)₂— | H | Cl | H | CF₃ | H | |
| 50 | 2-Decyl | Cl | H | H | CF₃ | H | |

*this compound melted with decomposition

EXAMPLE 51

6-Chloro-1,2,8,9-tetrahydro-9-oxopyrido[4',3':2,3]indolo[1,7-ab][1,4]benzodiazepin-3(4H)-butanoic acid hydrochloride (I, X=O; R=(CH₂)₃CO₂H, R₂=Cl, R₁=R₃=R₄=R₅=H; •HCl)

A mixture of 6-chloro-1,2,8,9-tetrahydro-9-oxopyrido[4',3':2,3]indolo[1,7-ab]benzodiazepin-3(4H)-butanoic acid, ethyl ester, (Example 9; 4.0 g) and 3 N hydrochloric acid (60 ml) was stirred and refluxed for 1 hour and then evaporated to dryness in vacuo. The residual semi-solid was boiled with a small quantity of 2-propanol, cooled and filtered to yield the title compound, m.p. 255°–258° (dec.).

A procedure similar to that of Example 51 is used to hydrolyze esters prepared by the alkylation procedure of Example 51 or the Michael addition procedure of Example 52.

EXAMPLE 52

5-Chloro-1,2,3,4-tetrahydro-3-(3-oxobutyl)-pyrido[4',3':2,3]indolo[1,7-ab][1,4]benzodiazepin-8(9H)-one (I, X=O; R=CH₂CH₂COCH₃; R₁=Cl, R₂=R₃=R₄=R₅=H)

Methyl vinyl ketone (1.2 g) was added in one lot to a warm solution of 5-chloro-1,2,3,4-tetrahydropyrido[4',3':2,3]indolo[1,7-ab][1,4]benzodiazepin-8(9H)-one (Example I; 4.8 g) in a mixture of tetrahydrofuran (100 ml) and dimethylformamide (150 ml) and the resulting mixture was stirred and refluxed for 2 hours and the concentrated to a small volume and poured into an excess of ice and water. The solid that separated was filtered off, washed with water and recrystallized from a mixture of 2-propanol and tetrahydrofuran to yield the title compound; m.p. 180°–182° (dec.).

The compound of Example 52, and other compounds which may be prepared by such a Michael addition procedure, are listed in Table IV.

TABLE IV

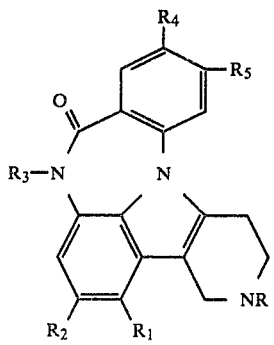

(X = O)

| Ex. | R | $R_1$ | $R_2$ | $R_3$ | $R_4$ | $R_5$ | m.p. (°C.) |
|---|---|---|---|---|---|---|---|
| 52 | $CH_2CH_2COCH_3$ | H | H | H | H | H | 180–182° |
| 53 | $CH_2CH_2COPh$ | H | Cl | H | H | H | |
| 54 | $CH_2CH_2CO(4\text{-}FC_6H_4)$ | H | H | Me | H | H | |
| 55 | $CH_2CH_2CO_2Me$ | H | H | H | Cl | H | |
| 56 | $CH_2CH_2CO_2Et$ | Cl | H | H | $CF_3$ | H | |
| 57 | $CH_2CH_2CN$ | H | $CF_3$ | H | H | Cl | |
| 58 | $CH_2CH_2CONMe_2$ | H | Cl | H | H | H | |

EXAMPLE 59

6-Chloro-1,2,3,4,8,9-hexahydropyrido[4′,3′:2,3]indolo[1,7-ab][1,4]benzodiazepine (I, $X=H_2$; $R_2=Cl$, $R=R_1=R_3=R_4=R_5=H$)

A solution of borane in THF (1 M, 90 ml) was added carefully to a stirred solution-suspension of 6-chloro-1,2,3,4-tetrahydropyrido[4′,3′:2,3]indolo[1,7-ab][1,4]benzodiazepin-9(8H)-one (Example I-3; 14.4 g) in tetrahydrofuran (200 ml) and the resulting mixture refluxed for 2 hours, cooled and the excess of borane destroyed by dropwise addition of 3 N hydrochloric acid. The mixture was then evaporated to dryness under reduced pressure and the residue refluxed with 3 N hydrochloric acid (200 ml) for 2 hours. Evaporation of the mixture to dryness under reduced pressure provided the salt of the title product which was taken up in a small quantity of water, basified with 10% aqueous sodium hydroxide and extracted thrice with methylene chloride. The combined methylene chloride extracts were washed with water, dried over anhydrous magnesium sulfate and stripped of the solvent under reduced pressure to yield the title product which was recrystallized from a mixture of 2-propanol and methanol, m.p. 210°–212°.

The compound of Example 59, substituted 1,2,3,4,8,9-hexahydropyrido[4′,3′:2,3]indolo[1,7-ab][1,4]benzodiazepines which were prepared by the foregoing procedure, and others which may be prepared by that procedure are listed in Table V.

TABLE V

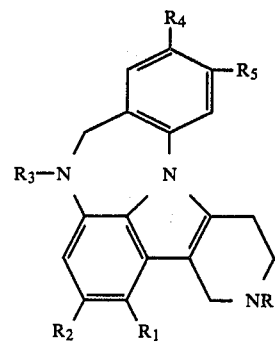

(X = $H_2$)

| Ex. | R | $R_1$ | $R_2$ | $R_3$ | $R_4$ | $R_5$ | m.p. (Solvent of Recrystallization) |
|---|---|---|---|---|---|---|---|
| 59 | H | H | Cl | H | H | H | 210–212° (2-PrOH/MeOH) |
| 60 | H | H | $CF_3$ | H | H | H | 273–275° (2-PrOH) |
| 61 | H | H | H | H | Cl | H | 136–137° (2-PrOH) |
| 62 | H | H | $CF_3$ | Me | H | H | 278–280° (2-PrOH)* |
| 63 | H | H | Cl | H | Cl | H | |
| 64 | H | Cl | H | H | H | H | |
| 65 | H | H | H | H | H | Cl | |
| 66 | H | H | Cl | H | $CF_3$ | H | |
| 67 | H | H | Et | H | Cl | H | |

*hydrochloride salt

EXAMPLE 68

6-Chloro-3-cyclohexylmethyl-1,2,3,4,8,9-hexahydropyrido[4′,3′:2,3]indolo[1,7-ab][1,4]benzodiazepine

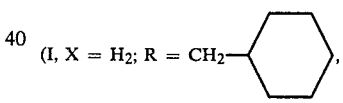

$R_2 = Cl$, $R_1 = R_3 = R_4 = R_5 = H$)

A solution of borane in tetrahydrofuran (1 M, 50 ml) was added carefully to a stirred solution-suspension of 6-chloro-3-cyclohexylcarbonyl-1,2,3,4-tetrahydropyrido[4′,3′:2,3]indolo[1,7-ab][1,4]benzodiazepin-9(8H)-one (3.0 g) in tetrahydrofuran (100 ml) and the resulting mixture refluxed for 2 hours, cooled and the excess of borane destroyed by dropwise addition of water. The mixture was then evaporated to dryness under reduced pressure and the residue refluxed with a mixture of 1-octene (50 ml) and xylene (80 ml) for 1 hour and xylene and the combined filtrates were evaporated under reduced pressure. The residue was triturated with a small quantity of ether, filtered, and recrystallized from a mixture of 2-propanol and ethanol to yield the title compound, m.p. 230°–233° (dec.).

The compound of Example 68, another hexahydropyridoindolobenzodiazepine prepared by essentially the foregoing procedure, and others that can be prepared by that procedure, are listed in Table VI.

TABLE VI

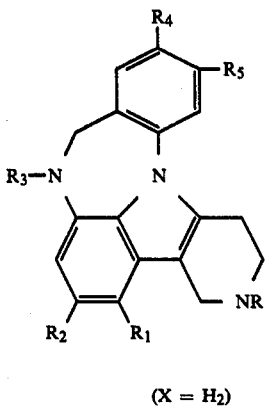

(X = H₂)

| Ex. | R | R₁ | R₂ | R₃ | R₄ | H | m.p.(°C.) |
|---|---|---|---|---|---|---|---|
| 68 | ⌬-CH₂ | H | Cl | H | H | H | 230–233° (d) |
| 69 | Ph(CH₂)₂ | H | H | H | Cl | H | 222–225° (d) |
| 70 | Et | Cl | H | H | Cl | H | |
| 71 | ▷-CH₂ | H | CF₃ | H | Me | H | |
| 72 | 1-Hexyl | H | Cl | H | H | H | |
| 73 | Adamantyl-(CH₂)₂ | H | H | H | CF₃ | H | |
| 74 | PhO(CH₂)₄ | H | H | Me | Cl | H | |

EXAMPLE 75

3-Ethoxycarbonyl-1,2,3,4-tetrahydro-8-methyl-6-trifluoromethylpyrido[4',3':2,3]indolo[1,7-ab]benzodiazepin-9(8H)-one (I', X=O; R'=OEt, R₂=CF₃, R₃=Me, R₁=R₄=R₅=H)

Sodium hydride (50% oil dispersion, 3.6 g) was added, in small portions, to a well-stirred solution of 3-ethoxycarbonyl-1,2,3,4-tetrahydro-6-trifluoromethylpyrido[4',3':2,3]indolo[1,7-ab]benzodiazepin-9(8H)-one (32.17 g) in dimethylformamide (500 ml). After the addition was complete the mixture was stirred and heated at 50° for 15 minutes and then cooled to room temperature and treated with methyl iodide (15.57 g), added dropwise. The mixture was stirred at room temperature for 2 hours, diluted with a large volume of cold water and extracted thoroughly with methylene chloride. The methylene chloride extract was washed repeatedly with water, dried over anhydrous magnesium sulfate and stripped of the solvent under reduced pressure. The residue was triturated with ether and filtered to provide the title compound, m.p. 212°–214° (dec.) which was pure enough for subsequent reactions. It was recrystallized from i-PrOH, m.p. 212°–214° (dec.).

EXAMPLE 76

1,2,3,4,8,9-Hexahydro-6-trifluoromethyl-3,8-dimethylpyrido[4',3':2,3]indolo[1,7-ab]benzodiazepine (I, X=H₂; R=Me, R₂=CF₃, R₃=Me, R₁=R₄=R₅=H)

A solution of 3-ethoxycarbonyl-1,2,3,4-tetrahydro-8-methyl-6-trifluoromethylpyrido[4',3':2,3]indolo[1,7-ab]benzodiazepin-9(8H)-one (7.92 g) in anhydrous tetrahydrofuran was added dropwise to a stirred one molar solution of lithium aluminum hydride (80 ml); after the addition was complete, the mixture was stirred and refluxed for 2 hours and cooled in an ice bath. The excess of lithium aluminum hydride in the mixture was then destroyed by dropwise addition of water with vigorous stirring. The mixture was filtered, the residue washed with tetrahydrofuran, and the combined filtrates dried over anhydrous magnesium sulfate and evaporated under reduced pressure. The residue was recrystallized from 2-propanol to yield the title compound, m.p. 212°–214°.

The procedure of Examples 75 and 76 can be applied to unsubstituted or otherwise substituted substrates to prepare hexahydropyridoindolobenzodiazepines (I, X=H₂) with other values of R₁, R₂, R₄, and R₅.

EXAMPLE 77

3-Acetyl-6-chloro-1,2,3,4-tetrahydropyrido[4',3':2,3]indolo[1,7-ab][1,4]benzodiazepin-9(8H)-one (I', X=O; R'=CH₃, R₂=Cl, R₁=R₃=R₄=R₅=H)

Acetyl chloride (1.7 g) was added in one lot to a stirred mixture of 6-chloro-1,2,3,4-tetrahydropyrido[4',3':2,3]indolo[1,7-ab][1,4]benzodiazepin-9(8H)-one (6.4 g), triethylamine (2.2 g) and dimethylformamide (100 ml). The mixture was then stirred and heated at 70° for 2 hours, cooled, and poured into an excess of ice and water containing 30 ml of concentrated hydrochloric acid. The solid that separated was filtered off, washed with water, boiled with a small quantity of 2-propanol, filtered and washed with 2-propanol and ether to yield the title compound, m.p. 265°–267° (dec.). It was recrystallized from methanol containing a little THF, m.p. 265°–267° (dec.).

The following compounds shown in Table VII, which includes the compound of Example 77, were prepared by an essentially similar procedure:

TABLE VII

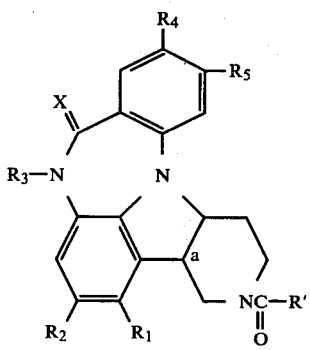

I', a = double bond
II', a = single bond

| Ex. | X | a | R' | R₁ | R₂ | R₃ | R₄ | R₅ | m.p. (Solvent of recrystallization) |
|---|---|---|---|---|---|---|---|---|---|
| 77 | O | double | Me | H | Cl | H | H | H | 265–267° (d)(MeOH) |
| 78 | O | double | Me | H | H | H | H | H | 233–235° (d)(EtOH) |
| 79 | O | double | Me | H | CF₃ | H | H | H | 295–297° (d)(MeOH) |
| 80 | O | double | Me | H | H | Me | H | H | 266—226° (d)(EtOH/MeOH) |
| 81 | O | double | Me | H | H | H | Cl | H | 263–265° (d)(THF/hex.) |
| 82 | O | double | Me | H | CF₃ | H | Cl | H | 314–317° (d)(THF/hex.) |
| 83 | O | double | Me | H | CF₃ | Me | Cl | H | 217–220° (d)(2-PrOH/MeOH) |
| 84 | O | double | EtO | H | H | H | H | H | 189–191° (2-PrOH) |
| 85 | O | double | EtO | H | CF₃ | H | H |  | 273–275° (d)(MeOH/THF) |
| 86 | O | double | EtO | H | H | Me | H | H | 150–152° (EtOH) |
| 87 | O | double | EtO | H | CF₃ | Me | H | H | 212–214° (2-PrOH) |
| 88 | O | double | 1-pentyl | H | Cl | H | Me | H | 185–188° (d)(THF/hex.) |
| 89 | O | double | ▷— | H | CF₃ | H | H | H | 295–297° (d)(THF) |
| 90 | O | double | ◯— | H | Cl | H | H | H | 183–185° (d)(MeOH/THF) |
| 91 | O | double | PhCH₂ | H | H | H | Cl | H | 145–148° (d)(2-PrOH) |
| 92 | O | double | ◯— | H | H | H | H | H | 252–255° (d) |
| 93 | O | double | PhCH₂ | H | H | H | Cl | H | 145–148° (d)(2-PrOH) |
| 94 | H₂ | double | EtO | H | Cl | CO₂Et | H | H | 151–153° (d) |
| 95 | H₂ | single | EtO | H | Cl | CO₂Et | H | H | 155–157° (2-PrOH) |

EXAMPLE 96 trans-6-Chloro-3-ethyl-1,2,3,4,4a,8,9,14a-octahydropyrido[4',3':2,3]indolo[1,7-ab][1,4]benzodiazepine, Dihydrochloride (II; R=Et, R₂=Cl, R₁=R₃=R₄=R₅=H; •2HCl)

A solution of borane in tetrahydrofuran (1 M, 150 ml) was added carefully to a stirred solution-suspension of 3-acetyl-6-chloro-1,2,3,4-tetrahydropyrido[4',3':2,3]indolo[1,7-ab][1,4]benzodiazpin-9(8H)-one (Example 77; 7.2 g) in tetrahydrofuran (300 ml) and the resulting mixture refluxed for 2 hours, cooled, and the excess of borane destroyed by the dropwise addition of 6 N hydrochloric acid. The mixture was then evaporated to dryness under reduced pressure and the residue refluxed with 6 N hydrochloric acid (100 ml) for 2 hours and evaporated to dryness again. The residue was taken up in a small quantity of water and basified with 10% aqueous sodium hydroxide and the mixture extracted twice with methylene chloride. The combined methylene chloride layers were washed with water, dried over anhydrous magnesium sulfate and stripped of the solvent under reduced pressure. The residue was dissolved in a small quantity of tetrahydrofuran and the solution added to an excess of absolute ether saturated with gaseous hydrogen chloride. The salt that separated was filtered off, washed with ether and recrystallized from methanol to provide the title compound, m.p. 275°–277° (dec.).

The following 1,2,3,4,4a,8,9,14a-octahydropyrido[4',3':2,3]indolo[1,7-ab][1H)benzodiazpines shown in Table VIII, which includes the compound of Example 96, were prepared by essentially the foregoing procedure.

TABLE VIII

| Ex. | R | R₁ | R₂ | R₃ | R₄ | R₅ | m.p. (Solvent of recrystallization) |
|---|---|---|---|---|---|---|---|
| 96+ | Et | H | Cl | H | H | H | 275–277° (d)(MeOH) |
| 97+ | Me | H | H | H | H | H | 195–200° (d)(2-PrOH/MeOH) |
| 98* | Me | H | Cl | H | H | H | 217–220° (d)(2-PrOH) |
| 99+ | Me | H | H | H | Cl | H | 235–237° (d)(2-PrOH) |
| 100* | Me | H | Cl | H | Cl | H | 215–220° (d)(2-PrOH) |
| 101 | Me | H | Cl | H | Me | H | 176–178° (Ether) |
| 102+ | Et | Cl | H | H | H | H | 270–273° (d)(2-PrOH) |
| 103+ | Et | H | CF₃ | H | H | H | 255–257° (d)(2-PrOH) |
| 104≠ | Et | H | H | Me | H | H | 172–174° (2-PrOH/EtOH) |
| 105 | Et | H | H | H | Cl | H | 151–153° (Hexane/THF) |
| 106+ | Et | H | Cl | Me | H | H | 210–212° (d)(2-PrOH/Ether) |
| 107≠ | Et | H | CF₃ | Me | H | H | 180–183° (d)(2-PrOH) |
| 108+ | 1-Hexyl | H | Cl | H | Me | H | 170–173° (d)(2-PrOH) |
| 109 | ▷—CH₂ | H | H | H | Cl | H | 187–189° |
| 110 | ▷—CH₂ | H | CF₃ | H | H | H | 173–175° (2-PrOH) |
| 111 | ⬡—CH₂ | H | H | H | H | H | 175–177° (2-PrOH) |
| 112 | PhCH₂ | H | H | Me | H | H | 160–165° (d)(2-PrOH) |
| 113* | Ph(CH₂)₂ | H | Cl | H | Me | H | 202–203° (d)(2-PrOH/MeOH) |
| 114+ | Ph(CH₂)₂ | H | H | H | Cl | H | 225–230° (d)(2-PrOH) |

*hydrochloride salt
+di-hydrochloride salt
≠maleate salt

EXAMPLE 115 trans-6-Chloro-1,2,3,4,4a,8,9,14a-octahydropyrido[4',3':2,3]indolo[1,7-ab][1,4]benzodiazpine (II, R₂=Cl, R=R₁=R₃=R₄=R₅=H)

Ethyl chloroformate (3.2 g) was added to a stirred mixture of trans-6-chloro-1,2,3,4,4a,8,9,14a-octahydro-3-methylpyrido[4',3':2,3]indolo[1,7-ab][1,4]benzodiazepine (Example 98; 8.6 g), tetrahydrofuran (200 ml) and anhydrous potassium carbonate (4.2 g) and the mixture refluxed for 3 hours, cooled and added to an excess of ice and water. The mixture was extracted with methylene chloride and the methylene chloride extract washed with water, dried over magnesium sulfate and evaporated under reduced pressure. The semi-solid residue was triturated with ether, filtered, and recrystallized from 2-propanol to yield trans-6-chloro-1,2,3,4,4a,8,9,14a-octahydro-3-methylpyrido[4',3':2,-3]indolo[1,7-ab][1,4]benzodiazepin-8-carboxylic acid ethyl ester, m.p. 195°–198°.

A stirred mixture of the above product (9.9 g), dioxane (200 ml) and sodium carbonate (2.0 g), to which ethyl chloroformate (2.6 g) was added last, was refluxed for 3 hours, cooled, and added to an excess of ice and water. The resulting mixture was extracted thrice with methylene chloride and the combined methylene chloride extracts were washed with water, dried over magnesium sulfate, and evaporated under reduced pressure. The highly viscous residual liquid was dissolved in a small quantity of methylene chloride and chromatographed over acid-washed alumina. Elution with a mixture of methylene chloride and ethyl acetate (1:1) furnished a solid which was recrystallized from 2-propanol to provide trans-6-chloro-1,2,3,4,4a,8,9,14a-octahydropyrido[4',3':2,3]indolo[1,7-ab][1,4]benzodiazepine-3,8-dicarboxylic acid, diethyl ester, m.p. 155°–157°.

A mixture of the above product (2.1 g), 1-butanol (80 ml) and powdered KOH (7.0 g) was stirred and refluxed for 3 hours, cooled and evaporated under reduced pressure. The residue was treated with cold water and extracted thrice with methylene chloride; the combined methylene chloride extracts were washed with water, dried over magnesium sulfate and evaporated under reduced pressure. The residual solid was recrystallized to provide the title compound, m.p. 213°–214°.

A procedure like that of Example 115 can be used to prepare compounds where R=H from 3-ethyl or 3-benzyl derivatives, as well. Substitution can be as desired at $R_1$, $R_2$, $R_3$, $R_4$, and $R_5$.

EXAMPLE 116

Preparation of
1,2,3,4-tetrahydropyrido[4',3':2,3]indolo[1,7-ab][1,4]benzodiazpin-9(8H)-thione-3-carboxylic Acid, Ethyl Ester (I'; X=S, R'=EtO, $R_1=R_2=R_3=R_4=R_5=H$)

Phosphorus pentasulfide (8.0 g) was added in one lot to a well-stirred solution of 1,2,3,4-tetrahydropyrido[4',3':2,3]indolo[1,7-ab][1,4]benzodiazepin-9(8H)-one-3-carboxylic acid, ethyl ester, (10.1 g) in anhydrous pyridine (120 ml) and the resulting mixture was stirred at reflux for 2 hours, cooled, and added to cold 6 N hydrochloric acid (120 ml). The solid that separated was filtered off, washed thoroughly with water and recrystallized from 2-propanol to yield the title compound, m.p. 205°–207° (d).

This tetrahydropyridoindolobenzodiazepin-9-thione can be transferred into Compounds I (X=S) by hydrolysis of the carbamate group according to the procedure in Example 115 and optional introduction of R groups at the 3-position according to procedures described above.

Other tetrahydropyridoindolobenzodiazepin-9-thiones, substituted as desired by $R_1$, $R_2$, $R_3$, $R_4$, and $R_5$, can be prepared by the above procedure starting with the appropriately substituted by tetrahydropyridoindolobenzodiazepin-9-ones.

Dosage Forms

The compounds of Formula I show tranquilizer activity in the mammalian central nervous system. These tranquilizing agents can be administered by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 200 milligrams per kilogram of body weight. Ordinarily 0.05 to 100, and preferably 0.1 to 50 milligrams per kilogram per day given in divided doses 2 to 4 times a day or in sustained release form is effective to obtain desired results. For the more potent compounds, e.g. trans-6-chloro-3-ethyl-1,2,3,4,4a,8,9,14a-octahydropyrido[4',3':2,3]indolo[1,7-ab][1,4]benzodiazepine (Example 96), the daily dosage ranges are about 0.01 to 100 milligrams per kilogram, preferably 0.05 to 50 milligrams per kilogram, and more preferably 0.1 to 25 milligrams per kilogram.

Dosage forms (compositions) suitable for internal administration contain from about 5 milligrams to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile and liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 25 milligrams of powdered active ingredient, 200 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 25 milligrams of the active ingredient. The capsules are washed and dried.

Tablets

A large number of tablets are prepared by conventional procedures so that the dosage unit is 25 milligrams of active ingredient, 7 milligrams of ethyl cellulose, 0.2 milligrams of colloidal silicon dioxide, 5 milligrams of magnesium stearate, 275 milligrams of microcrystalline cellulose, 11 milligrams of cornstarch and 123.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly-used techniques.

Suspension

An aqueous suspension is prepared for oral administration so that each 5 milliliters contain 5 milligrams of finely divided active ingredient, 200 milligrams of sodium carboxymethyl cellulose, 5 milligrams of sodium benzoate, 1.0 gram of sorbitol solution, U.S.P., and 0.025 milliliter of vanillin.

Injectable

A parenteral composition suitable for administration by injection is prepared by dissolving 1% by weight of active ingredient in sodium chloride injection U.S.P. XX and adjusting the pH of the solution to between 6 and 7. The solution is sterilized by commonly-used techniques.

Pharmaceutical Utility

The paradigm used for predicting tranquilizer activity was a Conditioned Avoidance Response (CAR) test in mice. Female white mice, 19–23 g, were used. The apparatus modified from Bovet, D. et al., Science, 163, 139–149 (1969), was a one-way shuttlebox with 0.4 mA scrambled electric footshock as unconditioned stimulus (US) and a 6 watt white light plus a relay buzzer as conditioned stimuli (CS). Mice were conditioned by three sets of 1–5 trials on day 1, then were fasted for 17–21 hours. The conditioned mice were tested for retention of the conditioned response on day 2, and then were dosed orally with test drug at doses such as 0, 1, 3, 9, 27 and 81 mg/kg. ED50 values (doses at which 50% of the animals would be expected to show response failure) were calculated by the moving average method [Thompson, W. R., Bact. Rev., 11, 115 (1947)]. Failure to avoid the CS at doses lower than the dose which blocked the US suggests probable tranquilizer activity.

The avoidance ED50's for compounds of this case are in Table IX.

TABLE IX

| Example No. | Mouse CAR ED$_{50}$ (mg/kg) |
| --- | --- |
| 1 | 17.1 / 27 |
| 2 | 39 |
| 3 | 45 |
| 4 | 29 |
| 5 | 81 |
| 6 | 24 |
| 7 | 25 |
| 8 | >54 |
| 9 | >81 |
| 10 | 19.7 |
| 11 | 67 |
| 12 | 12 |
| 13 | 10.5 |
| 14 | 31 |
| 16 | 47 |
| 17 | 37 |
| 18 | >81 |
| 19 | >81 |
| 20 | >81 |
| 21 | >81 |
| 31 | 23 |
| 32 | 27 |
| 33 | 21.7 |
| 34 | 13.6 |
| 35 | 56.2 |
| 36 | 52 |
| 37 | 11.8 |
| 38 | 56.2 |
| 40 | 47 |
| 41 | >81 |
| 42 | 162 |
| 43 | >81 |
| 44 | >162 |
| 51 | 56.2 |
| 52 | 39 |
| 59 | 9.0 |
| 61 | 34 |
| 62 | >81 |
| 68 | 7.1 |
| 69 | 27 |
| 96 | 0.3 |
| 97 | 9.0 |
| 99 | 1.4 |
| 100 | 2.1 |
| 101 | 0.69 |
| 102 | 5.8 |
| 103 | 1.2 |
| 104 | 41 |
| 105 | 24 |
| 106 | 5.8 |
| 107 | 10.1 |
| 108 | 2.5 |
| 109 | 2.1 |
| 110 | 15.6 |
| 111 | 3.3 |
| 112 | 6.8 |
| 113 | 3.5 |
| 114 | 5.2 |

What is claimed is:

1. A compound of the formula:

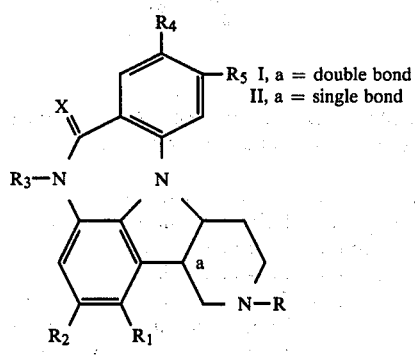

I, a = double bond
II, a = single bond wherein
a is a single or double bond; provided that when a is a single bond, the ring fusion is of the trans-configuration;
$R_1$, $R_2$, $R_4$ and $R_5$ independently are H, alkyl of 1 or 2 carbon atoms, $CF_3$, Cl, F or Br;
$R_3$ is H or alkyl of 1 to 3 carbon atoms;
R is H, alkyl of 1 to 10 carbon atoms, $(CH_2)_nC(O)R_6$, $(CH_2)_nCH(OH)R_6'$, $(CH_2)_nCONR_8R_9$, $(CH_2)_n(C_3$-$_7$ cycloalkyl), $(CH_2)_n$adamantyl,

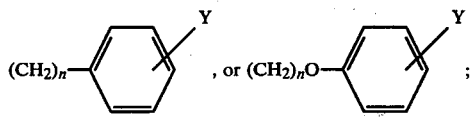

n is 1 to 8;
R$_6$ is H, OH, OR$_7$, C$_{1-3}$ alkyl, C$_{3-6}$ cycloalkyl, or

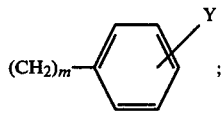

R$_6'$ is H, C$_{1-3}$ alkyl, C$_{3-6}$ cycloalkyl,

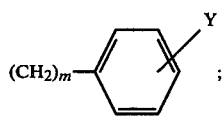

m is O to 3;
R$_7$ is CH$_3$ or C$_2$H$_5$;
Y is H, CH$_3$, OCH$_3$ or NO$_2$;
R$_8$ and R$_9$ are independently H, CH$_3$ or C$_2$H$_5$, or
R$_8$ and R$_9$, together, are —CH$_2$CH$_2$OCH$_2$CH$_2$—; and
X is H$_2$, O, or S, provided that when X is O or S, then a is a double bond; and provided further that when X is H$_2$, a is a single bond, and R$_1$, R$_4$ and R$_5$ are H, then R$_2$ cannot be CF$_3$ when R is CH$_3$ or

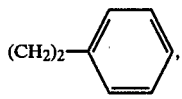

and R$_2$ cannot be Cl when R is

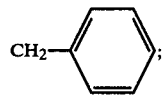

or a pharmaceutically acceptable salt thereof.

2. A compound of claim 1 wherein R is alkyl of 1 to 3 carbon atoms.
3. A compound of claim 1 wherein R$_1$ is H.
4. A compound of claim 1 wherein R$_2$ is Cl.
5. A compound of claim 1 wherein R$_3$ is H or CH$_3$.
6. A compound of claim 1 wherein R$_4$ is Cl.
7. A compound of claim 1 wherein R$_5$ is H.
8. A compound of claim 1 wherein a is a single bond.
9. A compound of claim 1 wherein X is H$_2$.
10. A compound of claim 9 wherein
R is alkyl of 1 to 3 carbon atoms;
R$_1$ is H;
R$_2$ is Cl;
R$_3$ is H or CH$_3$;
R$_4$ is Cl;
R$_5$ is H; and
a is a single bond.
11. A pharmaceutical composition consisting essentially of a pharmaceutically suitable carrier and a tranquilizing effective amount of a compound of claim 1, claim 2, claim 3, claim 4, claim 5, claim 6, claim 7, claim 8, claim 9 or claim 10.

12. A method for tranquilizing a mammal which comprises administering to a mammal in need of such treatment a tranquilizing effective amount of a compound of claim 1, claim 2, claim 3, claim 4, claim 5, claim 6, claim 7, claim 8, claim 9 or claim 10.

13. A compound of the formula:

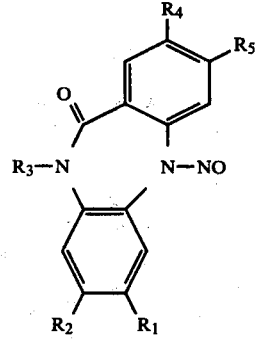

III where
R$_1$, R$_2$, R$_4$, and R$_5$ independently are H, alkyl of 1 or 2 carbon atoms, CF$_3$, Cl, F, or Br; and
R$_3$ is H, or alkyl of 1 to 3 carbon atoms.

14. A compound of the formula:

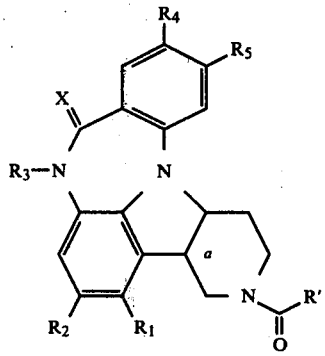

wherein
a is a single or double bond; provided that when a is a single bond, the ring fusion is of the trans-configuration;
R$_1$, R$_2$, R$_4$ and R$_5$ independently are H, alkyl of 1 or 2 carbon atoms, CF$_3$, Cl, F or Br;
R$_3$ is H, alkyl of 1 to 3 carbon atoms, or CO$_2$R$_7$; and
R' is OR$_7$, alkyl of 1 to 9 carbon atoms, (CH$_2$)$_{n-1}$(C$_{3-7}$ cycloalkyl), (CH$_2$)$_{n=1}$ adamantyl,

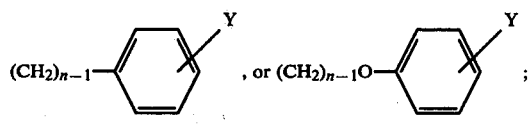

where n is 1 to 8;
R$_7$ is CH$_3$, or C$_2$H$_5$; and
Y is H, CH$_3$, OCH$_3$, or NO$_2$ and X is H$_2$, O or S, provided that when X is O or S, then a is a double bond, and provided further that when X is H$_2$, a is a single bond.

* * * * *